(12) United States Patent
Rabbani et al.

(10) Patent No.: US 11,066,694 B2
(45) Date of Patent: Jul. 20, 2021

(54) AFFINITY TAG NUCLEIC ACID AND PROTEIN COMPOSITIONS, AND PROCESSES FOR USING SAME

(71) Applicant: Enzo Biochem, Inc., New York, NY (US)

(72) Inventors: Elazar Rabbani, New York, NY (US); Jannis G. Stavrianopoulos, Bay Shore, NY (US); James J. Donegan, Long Beach, NY (US); Wayne Patton, Dix Hills, NY (US); Juan Carcamo, New York, NY (US)

(73) Assignee: Enzo Biochem, Inc., New York, NY (US)

( * ) Notice: Subject to any disclaimer, the term of this patent is extended or adjusted under 35 U.S.C. 154(b) by 0 days.

(21) Appl. No.: 16/225,244

(22) Filed: Dec. 19, 2018

(65) Prior Publication Data

US 2019/0382822 A1 Dec. 19, 2019

Related U.S. Application Data

(62) Division of application No. 15/209,906, filed on Jul. 14, 2016, now Pat. No. 10,196,672, which is a division of application No. 12/004,842, filed on Dec. 20, 2007, now abandoned.

(51) Int. Cl.
| | |
|---|---|
| *C12Q 1/68* | (2018.01) |
| *C07H 21/00* | (2006.01) |
| *C12Q 1/6804* | (2018.01) |
| *C12Q 1/6818* | (2018.01) |
| *C12Q 1/6834* | (2018.01) |
| *G01N 33/58* | (2006.01) |
| *G01N 33/68* | (2006.01) |
| *C12Q 1/6806* | (2018.01) |
| *G01N 33/53* | (2006.01) |

(52) U.S. Cl.
CPC ......... *C12Q 1/6804* (2013.01); *C12Q 1/6806* (2013.01); *C12Q 1/6818* (2013.01); *C12Q 1/6834* (2013.01); *G01N 33/58* (2013.01); *G01N 33/6854* (2013.01); *G01N 33/5308* (2013.01); *G01N 2458/10* (2013.01)

(58) Field of Classification Search
CPC .................................. C12Q 1/68; C07H 21/00
See application file for complete search history.

(56) References Cited

U.S. PATENT DOCUMENTS

| | | | |
|---|---|---|---|
| 4,707,440 A | 11/1987 | Stavrianopoulos et al. | |
| 4,711,955 A | 12/1987 | Ward et al. | |
| 4,877,830 A | 10/1989 | Dobeli et al. | |
| 4,894,325 A | 1/1990 | Englehardt et al. | |
| 4,908,453 A | 3/1990 | Cocuzza | |
| 5,124,246 A | 6/1992 | Urdea et al. | |
| 5,241,060 A | 8/1993 | Engelhardt et al. | |
| 5,284,933 A | 2/1994 | Dobeli et al. | |
| 5,484,909 A * | 1/1996 | Nietupski | C07H 21/00 435/252.9 |
| 5,545,522 A | 8/1996 | Van Gelder et al. | |
| 5,635,352 A * | 6/1997 | Urdea | C12Q 1/6813 435/6.18 |
| 5,843,663 A | 12/1998 | Stanley et al. | |
| 5,863,719 A | 1/1999 | Houghton et al. | |
| 6,251,639 B1 | 6/2001 | Kurn et al. | |
| 6,264,825 B1 * | 7/2001 | Blackburn | B82Y 15/00 205/777.5 |
| 6,316,229 B1 * | 11/2001 | Lizardi | C12Q 1/682 435/6.1 |
| 6,743,605 B1 | 6/2004 | Rabbani et al. | |
| 6,838,244 B1 | 1/2005 | Li et al. | |
| 6,982,146 B1 | 1/2006 | Schneider et al. | |
| 7,163,796 B2 | 1/2007 | Stavrianopoulos et al. | |
| 7,166,478 B2 | 1/2007 | Stavrianopoulos et al. | |
| 7,183,392 B2 | 2/2007 | Wagner et al. | |
| 7,247,434 B2 | 7/2007 | Van Ness et al. | |
| 7,309,567 B1 * | 12/2007 | Mathis | G01N 33/533 435/174 |
| 8,309,306 B2 * | 11/2012 | Nolan | C12Q 1/682 435/6.1 |
| 9,938,590 B2 * | 4/2018 | Pollner | C12Q 1/6837 |
| 10,196,672 B2 * | 2/2019 | Rabbani | C12Q 1/6806 |
| 2001/0055773 A1 * | 12/2001 | Jayasena | C12Q 1/6818 435/6.12 |
| 2002/0197606 A1 * | 12/2002 | Craig | G01N 33/573 435/6.13 |

(Continued)

FOREIGN PATENT DOCUMENTS

| | | |
|---|---|---|
| EP | 0 128 332 | 12/1984 |
| EP | 0 611 828 | 8/1994 |

(Continued)

OTHER PUBLICATIONS

Chaudri et al., FEB Letters 450: 23-26 (Year: 1999).*

(Continued)

*Primary Examiner* — Ethan C Whisenant
(74) *Attorney, Agent, or Firm* — Paul Diamond, Esq.

(57) ABSTRACT

The present invention concerns compositions and processes that use affinity tags for isolating, and detecting or quantifying analytes, including nucleic acids, proteins and polypeptides. Compositions include nucleic acid compositions and protein compositions with affinity binding pairs, including metal binding peptides and immobilized metals, or peptide affinity groups.

6 Claims, 3 Drawing Sheets
Specification includes a Sequence Listing.

(56) References Cited

U.S. PATENT DOCUMENTS

| | | | |
|---|---|---|---|
| 2003/0064395 A1* | 4/2003 | Chung | G01N 33/542 435/6.18 |
| 2003/0104620 A1 | 6/2003 | Engelhardt et al. | |
| 2003/0129611 A1* | 7/2003 | Bao | C12Q 1/6818 435/6.11 |
| 2003/0170230 A1* | 9/2003 | Caterer | C07K 17/06 424/130.1 |
| 2003/0235828 A1* | 12/2003 | Gillibolian | C12Q 2565/531 435/6.12 |
| 2004/0053300 A1* | 3/2004 | Soderlund | C12Q 1/6816 435/5 |
| 2004/0197866 A1 | 10/2004 | Johnson et al. | |
| 2004/0219523 A1 | 11/2004 | Stanton et al. | |
| 2005/0043507 A1 | 2/2005 | Campbell et al. | |
| 2005/0064414 A1* | 3/2005 | Hanna | C12Q 1/6858 435/6.15 |
| 2006/0068417 A1* | 3/2006 | Becker | C12Q 1/6837 435/6.11 |
| 2006/0094062 A1 | 5/2006 | Wu et al. | |
| 2006/0105341 A1* | 5/2006 | Krause | C12Q 1/6897 435/6.13 |
| 2006/0127920 A1* | 6/2006 | Church | C12Q 1/6846 435/6.16 |
| 2006/0141554 A1 | 6/2006 | Gee et al. | |
| 2006/0177836 A1 | 8/2006 | McKernan et al. | |
| 2006/0275282 A1* | 12/2006 | Moore | C07K 16/00 424/130.1 |
| 2006/0292438 A1* | 12/2006 | Greenfield | B82Y 10/00 429/63 |
| 2007/0172839 A1 | 7/2007 | Smith et al. | |
| 2009/0099029 A1* | 4/2009 | Samuels | C07K 14/4713 506/9 |
| 2009/0130680 A1* | 5/2009 | Yamamoto | G01N 33/5308 435/6.11 |
| 2009/0275142 A1* | 11/2009 | Huang | C07D 209/08 436/86 |
| 2014/0248710 A1* | 9/2014 | Heyduk | G01N 33/5308 436/501 |
| 2019/0382822 A1* | 12/2019 | Rabbani | C12Q 1/6834 |

FOREIGN PATENT DOCUMENTS

| | | |
|---|---|---|
| WO | WO2004016811 | 2/2004 |
| WO | WO2005080603 | 9/2005 |

OTHER PUBLICATIONS

Frieden et al., Chemistry & Biodiversity 1 : pp. 1-10 (Year: 2004).*
Gull berg et al., PNAS 101(22) : 8420 (Year: 2004).*
Marchan et al., Tetrahedron 60: 5461 (Year: 2004).*
Venkatesan et al., Chem. Rev. 106 : 3712 (Year: 2006).*
Cronan, John E. Biotination of Proteins in Vivo. J. of Biological Chemistry 265(18) : 10327-10333 (Year: 1990).*
Girault et al., Coupling of MALDI-TOF Mass Analysis to the Separation of Biotinylated Peptides by Magnetic Streptavidin Beads. Analytical Chemistry 68 :2122-2126 (Year: 1996).*
Hearn et al., Review : Applications of novel affinity cassette methods: use of peptide fusion handles for the purification of recombinant proteins. J. of Molecular Recognition 14 :323-369 (Year: 2001).*
Kimple et al., Overview of Affinity Tags for Protein Purification. Curr Protoc. Protein Sci. 73 Unit-9.9 (Year: 2015).*
Min et al. Immobilized metal affinity chromatography of DNA. Nucleic Acids Research 24(19) : 3806 (Year: 1996).*
Zuo et al., A novel sandwich assay with molecular beacon as report probe for nucleic acids detection on one-dimensional microfluidic beads array. Analytica Chimica Acta 587 : 9-13 (Year: 2007).*
Chaga et al., Natural poly-histidine affinity tag for purification of recombinant proteins on cobalt(II)-carboxymethylaspartate cross-linked agarose, Journal of Chromatography A 1999, 247-256, 864.
Pasquinelli et al., Design of affinity tags for one-step protein purification from immobilized zinc columns, Biotechnol. Prog. 2000, 86-91, 16.
Chaga et al., Natural poly-histidine affinity tag for purification of recombinant proteins on cobalt(II) . . . , Journal of Chromatography A,1999, 247-256, 864.
Cheng et al., Facile synthesis of metal-chelating peptides on chip for protein array, Bioorganic & Medicinal Chemistry Letters, 2004,1987-1990, 14.
Dela Cadena et al., The sequence HGLGHGHEQQHGLGHGH in the light chain of high molecular weight kininogen serves . . . , Protein Science,1992, 151-160, 1.
Herwald et al., Zinc dependent conformational changes in domain D5 of high molecular mass kininogen modulate contact activation, Eur. J. Biochem, 2001, 396-404, 268.
Pasquinelli et al., Design of affinity tags for one-step protein purification from immobolized zinc columns, Biotechnol. Prog., 2000, 86-91,16.
Pixley et al., Fine mapping of the sequences in domain 5 of high molecular weight kininogen (HK) interacting with . . . , Journal of Thrombosis and Haemostasis, 2003, 1791-1798, 1.
Min and Verdine, Immobilized metal affinity chromatography of DNA, Nucleic Acids Research, 1996, 3806-3810, vol. 24, No. 19.
Wingren et al., Microarrays based on affinity tagged single-chain Fv antibodies: sensitive detection of analyte in complex proteomes, Proteomics, 2005, 1281-1291, 5.
Madhi et al., "Mapping the Interaction between High Molecular Mass Kininogen and the Urokinase Plasminogen Activator Receptor,"*The Journal of biological Chemistry*, vol. 279, No. 16, pp. 16621-16628 (2004).

* cited by examiner

Chimeric constructs used for capture or signaling

Binding of labeled oligos to matrices

AFFINITY TAG NUCLEIC ACID AND PROTEIN COMPOSITIONS, AND PROCESSES FOR USING SAME

CROSS-REFERENCE TO RELATED APPLICATIONS

This application is a divisional of Ser. No. 15/209,906 filed on Jul. 14, 2016, which is a divisional of U.S. application Ser. No. 12/004,842 filed Dec. 20, 2007, the contents of each is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 19, 2018, is named ENZ-79-D1-D1-Application-SL.txt and is 3,838 bytes in size.

FIELD OF THE INVENTION

This invention relates to affinity tag compositions including affinity tag nucleic acids and proteins, and processes useful for isolating and detecting or quantifying species of a nucleic acid of interest, and other processes for modifying, isolating, detecting or quantifying proteins and analytes of interest.

All patents, patent applications, patent publications, scientific articles and the like, cited or identified in this application are hereby incorporated by reference in their entirety in order to describe more fully the state of the art to which the present invention pertains.

BACKGROUND OF THE INVENTION

For many purposes of manipulating or analyzing nucleic acids, the first important step is isolation of the nucleic acids from other cellular material. In this regard, the earliest methods were relatively crude methods using ethanol precipitation followed by phase partitioning with organic reagents. For instance, phenol has been widely used to separate DNA from cellular material while RNA is more commonly isolated using a guanidinium isothiocyanate/phenol/chloroform mixture. These methods do not depend on the particular sequences of the nucleic acids for their isolation, i.e., they are sequence independent and the basis of separation is strictly derived from general chemical properties of DNA and RNA.

More sophisticated methods were later developed that employed the particular sequences of the nucleic acids as an identifying feature for separation, thereby enabling the isolation of nucleic acids with selected sequences apart from other nucleic acids as well as from other cellular material. A notable example of this method is "hybrid capture" where a nucleic acid complementary to the sequence or sequences of interest is used to specifically hybridize to one or more target nucleic acids. At a later step, a tag on the capture probe is used to separate material that has hybridized to the capture probe from material that remained unhybridized. Examples of formats that exploit this methodology include beads with oligo T segments for isolation of polyA RNA, and strepavidin-coated microtitre plates that can bind biotinylated primers after amplification reactions. In either case, a moiety capable of binding the tag is fixed to a solid support, thus enabling a series of simple washing steps to remove nucleic acids lacking the sequences of interest. Thus, in one case, a nucleic acid sequence is added to the capture probe, and in the other case, one of the nucleotides is modified by the addition of a ligand. Unfortunately, these methods are disadvantaged by the slower kinetics of mixed phase hybridization in the first case and the low capacity engendered by the attachment of large bulky proteins to a solid matrix in the aforementioned biotin/strepavidin method.

While conceptually simple, the isolation and purification of proteins has been at the same time both easier and more problematic. Unlike nucleic acids that have similar chemical properties regardless of sequence differences, the variety of different amino acids and the existence of secondary and tertiary structures have allowed the application of various criteria to be used for isolation of a single species of protein. These criteria include differences in molecular weight, shape, salt solubility, net charge and polar versus nonpolar characteristics. Thus, for purification of any given protein, a series of separation steps can be carried out that will be unique to that particular protein. However, these standard methods of protein purification lack the advantages described earlier for isolation of unique nucleic acid sequences where essentially a single methodology can be applied to purification of any species of interest. Although this has remained true for most native proteins, the burgeoning field of recombinant DNA has allowed more flexibility in modifying desirable proteins such that they carry additional amino acid sequences that can be helpful during purification procedures. The most notable example of such methods is the histidine tag which has been added to either the carboxy or amino end of the coding sequence (Dobeli et al., U.S. Pat. No. 5,284,933). The important feature of this oligopeptide sequence is that it has an affinity for chelated metals, such that a matrix with immobilized metal can be used to bind any protein that has such a histidine tag (Dobeli et al., U.S. Pat. No. 4,877,830), a method commonly referred to as IMAC (Immobilized Metal Affinity Chromatography). Thus, a single isolation procedure can be used for a wide variety of proteins after the proteins have been suitably modified. Although oligohistidine is the best known example of an oligo peptide that can bind to an immobilized metal, other peptides have been described as well, including one that has the amino acid sequence HGGHHG [SEQ ID NO:1] (Cheng et al. 2004 Bio-organic & Medicinal Chemistry Letters 14; 1987-1990).

The use of non-nucleic acid affinity tags has also been used in conjunction with nucleic acids. For instance, Min and Verdine (1996 Nucleic Acids Research 24:3806-3810) have described a nucleic acid primer with modified bases at the 5' end with histidine moieties attached to the bases. As such, their primer does not contain an oligopeptide tag as described above, but rather the 5' end has been modified with a series of histaminyl purine residues. Extension of these primers in a PCR reaction allows collection of the PCR products by means of a chelated resin. No application is described in this publication, however, for using these constructs for either signal detection or analyte isolation.

Stanley et al. (U.S. Pat. No. 5,843,663) describe the use of affinity agents attached to peptide nucleic acids (PNAs). As described previously in Min and Verdine (1996), cited supra., the individual amino acids are attached to each nucleotide analog as opposed to a true oligohistidine capture agent. It also should be pointed out that this is not an example of a chimeric molecule consisting of a nucleic acid and an affinity tag because the peptide nucleic acid is actually a synthetic substitute for a nucleic acid. The backbones of the constructs described by Stanley et al. have an essentially homogeneous nature because both the subunits of the amino acid segment and the peptide nucleic acid analogue segment are joined together by a succession of peptide bonds to form a single polymeric molecule. The method described in this patent has drawbacks that are intrinsic to the use of peptide nucleic acids. Specifically, efficient synthesis is limited to only short PNA sequences and there is a high cost associated with the reagents used in PNA synthesis.

Soderlund et al. (U.S. Patent Appl. No. 20040053300) describe a method of determining the quantity of discrete polynucleotide analytes by the use of a pool of nucleic acid probes of various sizes. The probes hybridize to analytes that have been modified by the addition of an affinity tag (such as oligo histidine) to the base portion. After hybridization of the probes to analytes, complexes are isolated by virtue of the presence of the affinity agent in the analyte allowing binding to a matrix. In a subsequent step the bound probes are released and quantified, thus giving an indirect measurement of the amount of analytes present in a sample. In this particular instance, the analytes themselves have been covalently attached to an affinity agent.

Affinity binding pairs have also been used in conjunction with RNA molecules in Krause and Simmons (U.S. Patent Appl. No. 20060105341). In this application, the use of a so-called RNA "fusion" molecule with "RNA tags" is described. In this particular case, however, the "fusion" is not RNA linked to a non-nucleic acid but rather the molecule is a fusion of different nucleic acid sequences resulting in a homogenous nucleic acid where a first RNA segment with a protein binding sequences is appended to a second RNA segment with a selected nucleic acid sequence. This second RNA segment may bind, in turn, to a fusion protein with two domains where one domain binds the RNA tag and the other domain can be an affinity partner, such as an oligo-His tag, that can be used to bind the RNA protein complex to a matrix. This composition has been used for identification and purification of RNA protein complexes and it has not been used for signal generation or isolation of nucleic acid analytes.

Histidine has also been used for other purposes besides an affinity label. For example, Van Ness et al. (U.S. Pat. No. 7,247,434) describe methods for simultaneously determining a number of different nucleic acid sequences by the use of tagged nucleic acid fragments. Sequences are derived from the association of a different tag for each nucleotide base incorporated into nucleic acids synthesized from analyte templates. In one particular instance, a single histidine moiety is used as one of the base-specific tags where identification is carried out by mass spectrometry after the nucleic acids have been separated by length. In this particular instance the histidine is not being used as an affinity agent but only as an identifier tag.

Many of the drawback in the previous uses of affinity tags such as histidine tags are overcome by the present invention.

SUMMARY OF THE INVENTION

This invention provides a composition which comprises a nucleic acid and one member of an affinity binding pair, wherein the member is attached to one or more nucleotides of the nucleic acid through a phosphate or sugar of the nucleotide or nucleotides.

This invention also provides a composition just described wherein the affinity binding pair comprises: (a) a metal binding peptide and an immobilized metal, or (b) a peptide affinity group.

This invention additionally provides a chimeric nucleic acid comprising at least two portions, a first portion comprising a nucleic acid complementary to a nucleic acid sequence of interest, and a second portion comprising a metal binding peptide, wherein the metal binding peptide is attached to one or more nucleotides of the nucleic acid in the first portion through a sugar or phosphate of the nucleotide or nucleotides.

Also provided by this invention is a chimeric nucleic acid comprising at least two portions, a first portion comprising a nucleic acid complementary to a nucleic acid sequence of interest, and a second portion comprising one member of a peptide affinity group, wherein the member is attached to one or more nucleotides of the nucleic acid in the first portion.

The present invention provides a process for isolating one or more species of a nucleic acid of interest. Various steps are used including the first step of providing a sample containing or suspected of containing the nucleic acid of interest, a composition which comprises a nucleic acid portion and a first member of an affinity binding pair, wherein the nucleic acid portion comprises sequences complementary to the nucleic acid species of interest, wherein the affinity binding pair comprises (a) a metal binding peptide and an immobilized metal, or (b) a peptide affinity group; and wherein the first member of the affinity binding pair is attached to one or more nucleotides in the nucleic acid portion; and a matrix comprising a second member of the affinity binding pair. The composition hybridizes with any nucleic acid of interest contained in the sample to form a first complex. The first complex is contacted with the matrix to form a second complex by means of a binding interaction between the first member and the second member of the affinity binding pair. Bound material is separated from unbound material, thereby isolating the nucleic acid species of interest.

The present invention also provides a process for detecting the presence or quantity of a nucleic acid of interest. In an initial step, the following elements are provided: a sample containing labeled nucleic acids, a composition comprising a nucleic acid portion and a first member of an affinity binding pair, wherein the nucleic acid portion comprises sequences complementary to the nucleic acid of interest, and a matrix comprising a second member of the affinity binding pair; wherein the affinity binding pair comprises (a) a metal binding peptide and an immobilized metal, or (b) a peptide affinity group; and wherein the first member of the affinity binding pair is attached to one or more nucleotides of the nucleic acid portion. The composition is allowed to hybridize with any nucleic acid of interest contained in the sample to form a first complex. This first complex is contacted with the matrix to form a second complex by means of a binding interaction between the first member and the second member of the affinity binding pair. The matrix is washed to remove unhybridized nucleic acids from the matrix. Detecting or quantifying the nucleic acid of interest is carried out by means of detecting or quantifying a signal from the labels.

The present invention provides yet another process for detecting the presence or quantity of a nucleic acid of interest. Various steps are performed including the initial step of providing the following elements: a sample containing or suspected of containing the nucleic acid of interest; a labeled probe complementary to the nucleic acid of interest; a composition comprising a nucleic acid portion and a first member of an affinity binding pair, wherein the nucleic acid portion comprises sequences complementary to the nucleic acid of interest, wherein the affinity binding pair comprises (a) a metal binding peptide and an immobilized metal, or (b) a peptide affinity group, and wherein the first member of the affinity binding pair is attached to one or more nucleotides of the nucleic acid portion through a sugar, phosphate or base of the nucleotide or nucleotides; and a matrix comprising a second member of the affinity binding pair. Any nucleic acids of interest in the sample are allowed to hybridize with labeled probe and the composition to form a first complex. This first complex is contacted with the matrix to form a second complex by means of a binding interaction between the first member and the second member of the affinity binding pair. The matrix is washed to remove unbound materials from the sample. The nucleic acid of interest is detected or quantified by means of detecting or quantifying a signal from the labels.

Yet another process provided by the present invention is one for detecting the presence or quantity of a nucleic acid of interest. Various steps are performed including the initial step of providing a sample containing or suspected of containing nucleic acid of interest; a probe complementary to the nucleic acid of interest and comprising two portions, wherein a first comprises sequences complementary to the nucleic acid of interest, and a second portion comprising a signal sequence; a composition comprising a nucleic acid portion and a first member of an affinity binding pair, wherein the nucleic acid portion comprises sequences complementary to the nucleic acid of interest, wherein the affinity binding pair comprises (a) a metal binding peptide and an immobilized metal, or (b) a peptide affinity group, and wherein the first member of the affinity binding pair is attached to one or more nucleotides of the nucleic acid; and a matrix comprising a second member of the affinity binding pair. Any nucleic acids of interest in the sample are hybridized with labeled probe and the composition to form a first complex. The first complex is contacted with the matrix to form a second complex by means of a binding interaction between the one or more binding partners and the affinity peptide. The matrix is washed to remove unbound materials from the sample. The nucleic acid of interest is detected or quantified by hybridizing labeled oligonucleotides complementary to the signal sequence.

The present invention also provides a fusion protein comprising a biologically active polypeptide or protein and at least one affinity peptide attached to the amino-terminus or the carboxyl-terminus of the biologically active polypeptide or protein, wherein the affinity peptide comprises at least a portion of the amino acid sequence of kininogen, such portion comprising a metal binding peptide.

The present invention additionally provides a fusion protein comprising a biologically active polypeptide or protein and an affinity peptide attached at the amino-terminus and an affinity peptide attached at the carboxyl-terminus of the biologically active polypeptide or protein, wherein the affinity peptides comprise at least a portion of the amino acid sequence kininogen, such portion comprising a metal binding peptide.

Another composition provided by this invention is a fusion protein comprising an antibody linked by its amino- and/or carboxyl-terminus to one or two affinity peptides, wherein the affinity peptide binds to a metal, and wherein the antibody has an affinity to an epitope on a different antibody.

The invention herein provides a process for modifying a protein of interest, this process comprising the steps of first providing (i) a nucleic acid that codes for the protein of interest; (ii) a nucleic acid that codes for a portion of the amino acid sequence of kininogen, wherein that portion codes for a metal binding peptide; and (iii) an expression vector. The nucleic acid (ii) is added to said nucleic acid (i) to generate a nucleic acid coding for a fusion protein. The nucleic acid coding for the fusion protein is inserted into the expression vector (iii), thereby generating a vector that expresses the modified protein of interest.

Additionally the invention herein provides a process for isolating a protein of interest, and this process comprises an initial step of providing: (i) a nucleic acid that codes for the protein of interest; (ii) a nucleic acid that codes for a portion of the amino acid sequence of kininogen, wherein the portion codes for a metal binding peptide; (iii) an expression vector; and (iv) a metal-modified matrix. Other steps include adding the nucleic acid (ii) to the nucleic acid (i) to generate a nucleic acid coding for a fusion protein, and inserting the nucleic acid coding for the fusion protein into the expression vector (iii), thereby generating a vector that expresses the protein of interest. Finally, the modified protein of interest is purified by binding the protein of interest to the metal-modified matrix (iv).

Other compositions are provided by the present invention including a fusion protein comprising an antibody and at least one affinity peptide attached to the amino terminus or the carboxyl terminus of the antibody, wherein the affinity peptide comprises a metal binding peptide or is one member of a peptide affinity group, wherein the antibody has an affinity for a different antibody.

Yet another fusion protein provided by this invention is one comprising an antibody and an affinity peptide attached to the amino terminus and an affinity peptide attached to carboxyl terminus of the antibody, wherein the affinity peptide comprises a metal binding peptide or is one member of a peptide affinity group, wherein the antibody has an affinity for a different antibody.

The invention herein also provides a process for isolating an analyte of interest, the process comprising the initial step of providing (i) a sample containing or suspected of containing the analyte of interest; (ii) a first antibody having an affinity for the analyte; (iii) a fusion antibody comprising: (a) an antibody and at least one affinity peptide attached to the amino terminus or the carboxyl terminus of the antibody, wherein the affinity peptide comprises a metal binding peptide or is one member of a peptide affinity group, wherein the antibody has an affinity for a different antibody; or (b) an antibody and an affinity peptide attached to the amino terminus and an affinity peptide attached to carboxyl terminus of the antibody, wherein the affinity peptide comprises a metal binding peptide or is one member of a peptide affinity group, wherein the antibody has an affinity for a different antibody; and (iv) a matrix comprising a metal or a second member of the affinity peptide group. The sample is contacted with the first antibody, thereby forming a first complex between the first antibody and any analyte present in the sample. The first complex is complexed with the fusion antibody, thereby forming a second complex between the first complex and the fusion antibody. The second complex is contacted with the matrix to bind the second complex to the matrix. Unbound material is removed from the matrix. The analyte of interest is released from the second complex, thereby isolating the analyte of interest.

Another process provided by this invention is one for detecting or quantifying an analyte of interest, said process comprising various steps. The first step provides (i) a labeled sample containing or suspected of containing labeled analyte of interest; (ii) a first antibody having an affinity for the analyte; (iii) a fusion antibody comprising: (a) an antibody and at least one affinity peptide attached to the amino terminus or the carboxyl terminus of the antibody, wherein the affinity peptide comprises a metal binding peptide or is one member of a peptide affinity group, wherein the antibody has an affinity for a different antibody; or (b) an antibody and an affinity peptide attached to the amino terminus and an affinity peptide attached to carboxyl terminus of the antibody, wherein the affinity peptide comprises a metal binding peptide or is one member of a peptide affinity group, wherein the antibody has an affinity for a different antibody; and (iv) a matrix comprising a metal or a second member of the affinity peptide group. The sample is contacted with the first antibody, thereby forming a first complex between the first antibody and any analyte present in the sample. The first complex is contacted with the fusion antibody, thereby forming a second complex between the first complex and the fusion antibody. The second complex is contacted with the matrix to bind the second complex to the matrix. Unbound material is removed from the matrix. Labeled analytes bound to the matrix are detected or quantified by means of detecting or quantifying a signal from the labels.

Yet another process provided herein is one for detecting or quantifying an analyte of interest, the process comprising various steps including the first step of providing (i) a labeled sample containing or suspected of containing labeled analytes of interest; (ii) a first antibody having an affinity for the analyte; (iii) a fusion antibody comprising: (a) an antibody and at least one affinity peptide attached to the amino terminus or the carboxyl terminus of the antibody, wherein the affinity peptide comprises a metal binding peptide or is one member of a peptide affinity group, wherein the antibody has an affinity for a different antibody; or (b) an antibody and an affinity peptide attached to the amino terminus and an affinity peptide attached to carboxyl terminus of the antibody, wherein the affinity peptide comprises a metal binding peptide or is one member of a peptide affinity group, wherein the antibody has an affinity for a different antibody; and (iv) a matrix comprising a metal or a second member of the affinity peptide group. A first complex is formed among the matrix, the fusion antibody and the first antibody. The first complex is contacted with the labeled sample, thereby forming a second complex between the first complex and any labeled analytes that may be present in the sample. Unbound material is removed from the matrix. The labeled analytes bound to the matrix are detected or quantified by means of detecting or quantifying a signal from the labels.

DESCRIPTION OF THE FIGURES

FIG. 1A illustrates a chimeric construct with a first portion consisting of a nucleic acid complementary to a chosen nucleotide sequence and a second portion with an oligohistidine portion used to bind nucleic acids with the chosen sequences to a solid matrix thereby allowing isolation of either nucleic acids that bind to the matrix or nucleic acids that lack complementarity to the construct.

FIG. 1B depicts a format where a chimeric construct similar to the one in FIG. 1A is used to detect the presence of the complementary sequence when a collection of labeled analytes are allowed to hybridize to the construct.

FIG. 1C shows a chimeric construct similar to the one in FIG. 1A that is used to detect the presence of unlabeled analytes by means of a probe complementary to the sequence of interest.

FIG. 1D illustrates a chimeric construct having energy transfer elements where hybridization of an analyte labeled with energy transfer elements provides signal generation that is dependent upon hybridization of the analyte to the construct.

FIG. 1E is a depiction of a format where energy transfer takes place between a labeled analyte and a signal probe.

FIG. 1F is a depiction of a format where the analyte is unlabeled and analyte specific energy transfer takes place between a signal probe and a chimeric construct.

FIG. 2A shows binding and elution of labelled chimeric constructs with Ni column.

FIG. 2B shows binding of labelled chimeric constructs with a 96 well plate.

DETAILED DESCRIPTION OF THE INVENTION

Figure 1A:
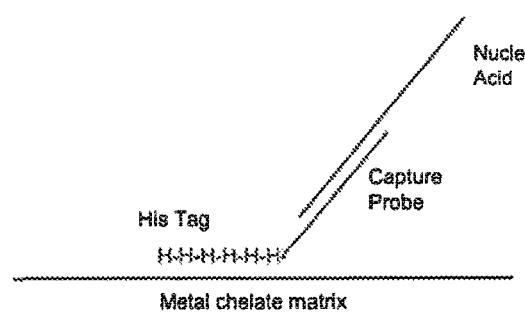
FIGS. 1A-F depict various formats that could be used with chimeric primers, as follows.

This invention provides a composition which comprises a nucleic acid portion that provides specific hybridization to a nucleic acid analyte of interest and a non-nucleic acid portion that comprises at least one member of an affinity binding pair that allows capture of the composition to a solid matrix wherein the member is attached to one or more nucleotides of the nucleic acid and this attachment can be through the phosphate, sugar or base of the nucleotide or nucleotides. Among such affinity binding pairs contemplated by this invention are pairs comprising an immobilized metal and a peptide or oligopeptide that has an affinity for such a metal.

Thus, the present invention provides a composition which comprises a nucleic acid and one member of an affinity binding pair, wherein the member is attached to one or more nucleotides of the nucleic acid through a phosphate or sugar of the nucleotide or nucleotide, and such attachment to such nucleotide or nucleotides can be through a linker arm as described further below. Furthermore, in the present composition and invention, the affinity binding pair comprises: (a) a metal binding peptide and an immobilized metal, or (b) a peptide affinity group. In a preferred embodiment the metal is immobilized by chelation. In the present invention, a peptide or oligopeptide is defined as a succession of amino acids joined through peptide bonds. Examples of metals that may be bound by such peptides are nickel, copper, cobalt and zinc. Examples of such peptides are oligohistidine and an oligopeptide with the sequence HGGHHG (SEQ ID NO:1) that have been referred to earlier. Other such oligopeptides that may be of use can include SPHHG (SEQ ID NO:2), SPHHGGSPHHG (SEQ ID NO:3), HPHHG (SEQ ID NO:4), HPHHGGHPHHG (SEQ ID NO:5), SPHHGGHPHHG (SEQ ID NO:6), and HPHHGGSPHHG (SEQ ID NO:7) described by Pasquinelli et al., 2000 (Biotechnol. Prog. 16, 86-91), KDHLIHNVHKEEHAHAHNK (SEQ ID NO:8) described by Chaga et al., 1999 (J. Chromatog A. 864; 247-256) as well as sequences derived from domain 5 of kininogen such as HGLGHGHEQQHGLGHGH (SEQ ID NO:9) and GHGLGHGHEQQHGLGHGHK [SEQ ID NO:10] (DeLa Cadena et al., 1992 Protein Science 1; 151-160; Pixley et al., 2003 J Thrombosis and Haemostasis 1; 1791-1798; and Herwald et al., 2001 Eur J Biochem 268; 396-404), all of which are incorporated by reference. Thus, the metal binding peptide can comprise any of the aforementioned amino acid sequences: oligohistidine, HGGHHG (SEQ ID NO:1), SPHHG (SEQ ID NO:2), SPHHGGSPHHG (SEQ ID NO:3), HPHHG (SEQ ID NO:4), HPHHGGHPHHG (SEQ ID NO:5), SPHHGGHPHHG (SEQ ID NO:6), HPHHGGSPHHG (SEQ ID NO:7), KDHLIHNVHKEE-HAHAHNK (SEQ ID NO:8), GHGLGHGHEQQHGLGHGHK (SEQ ID NO:10), or HGLGHGHEQQHGLGHGH (SEQ ID NO:9).

Other affinity binding pairs that may find use with the present invention can include peptide affinity pairs. In the present invention a peptide affinity pair is defined as any binary combination of peptides, oligopeptides or proteins that that are capable of recognizing and binding to each other. Examples of such pairs can include but are not necessarily limited to pairs such as: S-protein and S-peptide; Glutathione S-Transferase (GST) tag and Glutathione (GSH); Protein Kinase A catalytic subunit (PKA) recognition peptide and PKA; Hemagglutinin (HA) epitope tag peptide and HA, Ketosteroid Isomerase (KSI) tag and oligo Phe; KSI and oligo Leu; as well as "complementary" pairings such as oligo Arg with oligo Glu, and oligo Arg with oligo Asp. Thus, as used herein, the peptide affinity group can comprise: S-protein and S-peptide; GST and GSH; PKA recognition peptide and PKA; HA peptide epitope tag and HA; KSI and oligo PHE; KSI and oligo Leu; oligo Arg and oligo Glu; or oligo Arg and oligo Asp. A more complete discussion of these binding pairs is included in U.S. Pat. No. 7,183,392, incorporated herein by reference.

One member of the affinity binding pair will comprise part of a chimeric construct joined to a nucleic acid while the corresponding member of the pair is affixed or immobilized to a matrix. It is also understood that either member of a pair may be used as the non-nucleic acid portion such that it can be used with its corresponding member on the matrix. Thus, for instance, a chimeric nucleic acid can comprise an oligohistidine portion for capture by metal chelates attached to a solid matrix (an IMAC column or plate), or on the other hand, a nucleic acid can be used that has been modified by the presence of one or more metals allowing capture on a matrix comprising oligohistidine or some other metal binding peptide.

The chimeric nucleic acid provided by the present invention can comprise at least two portions, a first portion comprising a nucleic acid complementary to a nucleic acid sequence of interest, and a second portion comprising a metal binding peptide, e.g., nickel, copper, cobalt or zinc. The metal binding peptide can be attached, desirably through a linker arm as previously described, to one or more nucleotides of the nucleic acid in the first portion through a sugar or phosphate of the nucleotide or nucleotides. As described elsewhere in this disclosure, the metal binding peptide can comprise any of the amino acid sequences: oligohistidine, HGGHHG (SEQ ID NO:1), SPHHG (SEQ ID NO:2), SPHHGGSPHHG (SEQ ID NO:3), HPHHG (SEQ ID NO:4), HPHHGGHPHHG (SEQ ID NO:5), SPHHGGHPHHG (SEQ ID NO:6), HPHHGGSPHHG (SEQ ID NO:7), KDHLIHNVHKEEHAHAHNK (SEQ ID NO:8), GHGLGHGHEQQHGLGHGHK (SEQ ID NO:10), or HGLGHGHEQQHGLGHGH (SEQ ID NO:9). One or more energy transfer donors or one or more energy transfer acceptors can be incorporated into or attached to the chimeric nucleic acid just described.

Another chimeric nucleic acid provided by the present invention comprises at least two portions, a first portion comprising a nucleic acid complementary to a nucleic acid sequence of interest, and a second portion comprising one member of a peptide affinity group. The member can be attached, using a linker arm desirably, to one or more nucleotides of the nucleic acid in the first portion. As previously described, the peptide affinity binding group includes any of the pairs: S-protein and S-peptide, GST and GSH, PKA peptide and PKA, HA peptide and HA, KSI and oligo PHE, KSI and oligo Leu, oligo Arg and oligo Glu, or oligo Arg and oligo Asp. This additional embodiment of a chimeric nucleic acid can also further comprise one or more energy transfer donors, or one or more energy transfer acceptors.

Synthesis of the chimeric composition can be carried out by a variety of means where either the base, sugar or phosphate position of a nucleotide in the nucleic acid portion is used to attach the affinity agent. Examples of means of modifying nucleic acids that may be used for this purpose are described in Ward et al. in U.S. Pat. No. 4,711,955, Engelhardt et al., in U.S. Pat. No. 5,241,060, Stavrianopoulos et al., in U.S. Pat. No. 4,707,440, Pergolizzi et al., in EP 0 611 828 and Engelhardt et al., in U.S. Patent Application No. 20030104620, all of which are incorporated by reference. Attachment can be by means of a covalent attachment of one of the foregoing metals, oligopeptides or proteins to the nucleic acid portion, or it may be by means of noncovalent attachment through a secondary binding pair such as avidin and biotin. As an example of the latter, one of the proteins described above as a member of an affinity pair can be biotinylated using standard methods and the nucleic acid can be covalently linked to strepavidin. Formation of a complex between these two entities will create chimeric molecule comprising the affinity member and a nucleic acid portion.

Covalent attachment may be direct where the affinity agent is attached by itself to the nucleic acid portion or it may involve indirect covalent attachment where there is a linker arm joining the affinity agent to the nucleic acid portion. The position of attachment of the non-nucleotide portion to the nucleic acid can involve any chosen nucleotide; i.e., either internal or terminal nucleotides are suitable for carrying out the present invention. Linker arms are well-known in the art and have been described by a number of authors and researchers. See, for example, Ward et al. in U.S. Pat. No. 4,711,955, Engelhardt et al., in U.S. Pat. No. 5,241,060, Engelhardt et al., in U.S. Pat. No. 4,894,325, and Stavrianopoulos et al., in U.S. Pat. No. 7,186,478, all of which are incorporated herein by reference.

By means of the present invention, the presence of the nucleic acid portion will allow the capture of a nucleic acid and binding of it to a matrix through the affinity agent. The species of interest can be as broad or as narrow as the user desires by the appropriate choice of sequences used for the nucleic acid portion. For instance, the sequence can be selective for a single species such as a nucleic acid coding for a particular gene, or it may represent an entire class of molecules. Selectivity can be carried out with a single sequence in a chimeric composition or there may be more than one selective sequence in the chimeric composition. It is also envisioned that selectivity for different sequences may be carried out either sequentially or in parallel by having different selective sequences as part of separate chimeric compositions.

As such, sequences in the nucleic acid portion can comprise generic sequences such as oligo T or oligo A that can bind to a wide variety of different nucleic acids or the nucleic acid portion may comprise unique sequences that will bind to specific mRNA or cDNA species. An illustration of a possible means of carrying this out is shown in FIG. 1A. This aspect of the present invention may be used for either positive or negative selection. As an example of positive selection, the nucleic acid portion may comprise oligo or poly T sequences allowing the subsequent binding of polyA mRNA. Since mRNA generally consists of only 3-6% of total RNA, the subsequent removal of RNA unable to bind to a matrix bound chimeric construct results in a powerful enrichment of the poly A sequences that may be then used for a variety of purposes. As an example of negative selection, the majority of total RNA consists of rRNA sequences and these may be removed by the use of chimeric molecules that comprises sequences complementary to rRNA. After binding of complexes to a matrix, the portion of the total RNA that contains mRNA, hnRNA, µRNA and snRNA remains unbound, thereby allowing any and all of these species to be used in further steps. This may be of special use and significance when the foregoing analytes are desirable as labeled nucleic acids and the rRNA itself is of no use or interest. In such cases, the presence of the rRNA may even be deleterious since it may consume reagents and contribute noise to analytic methods, as seen for example, when total RNA is labeled by photobiotin, 94-97% of the labeled material would be irrelevant to analysis of polyA mRNA.

Figure 1B:
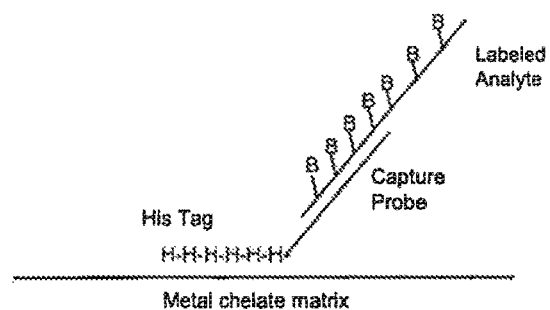

The nucleic acids of the present invention may also be used in a number of different ways: as part of a detection system; where a label may be included as part of the composition itself; when the analyte is being detected or quantified; or when a probe recognizes the analyte or combinations thereof. For instance, nucleic acid analytes from biological samples may be labeled directly by modifying the base, sugar or phosphate moieties. On the other hand, analytes may also be labeled during the course of copying or in amplification procedures where labeled nucleotides are provided during the course of such procedures, thereby synthesizing labeled complementary or identical copies of the original analytes. A chimeric composition could be used as a primer to generate a labeled complementary copy that may be subsequently isolated afterwards by means of the second member of the affinity pair or a normal primer could be used preparation of the labeled complementary copies where a hybridization with a chimeric composition is carried out afterwards. An example of a copying reaction that may find use in the present invention could be the use of samples containing mRNA where labeled cDNA copies are prepared by means of reverse transcriptase or a DNA polymerase with reverse transcriptase activity. A general depiction of this type of format is shown in FIG. 1B.

In principle, the same methods can be applied to amplification reactions where there are a series of copying reactions. Examples of amplification systems that may be useful in the present invention can include but are not necessarily limited to the polymerase chain reaction (PCR), ligase chain reaction (LCR), transcription mediated amplification (TMA), Strand displacement amplification (SDA), Nucleic acid sequence based amplification (NASBA) and Secondary Structure Amplification (Rabbani et al., in U.S. Pat. No. 6,743,605) all of which are incorporated by reference. Amplifications may be directed towards specific nucleic acid sequences as is generally used in the preceding methods, or there may be a more global amplification of multiple sequences from a library that includes the preceding methods as well as methods such as those taught by Van Gelder et al., in U.S. Pat. No. 5,545,522, Kurn in U.S. Pat. No. 6,251,639 and Stavrianopoulos et al., in U.S. Pat. No. 7,163,796, all of which are incorporated by reference. The synthesis of nucleic acids may take place after the nucleic acid(s) of interest have been isolated from a biological sample and released from a matrix or the reactions may take place while the nucleic acids are still bound to the matrix. In the latter case, the nucleic acids of the present invention may be used in a passive manner where they are only used to immobilize a nucleic acid in an environment where nucleic acid synthesis reactions may take place. Alternatively, it may be an active participant where the chimeric nucleic acid comprises a promoter or acts as a primer in reactions such as those cited above.

Figure 1C:
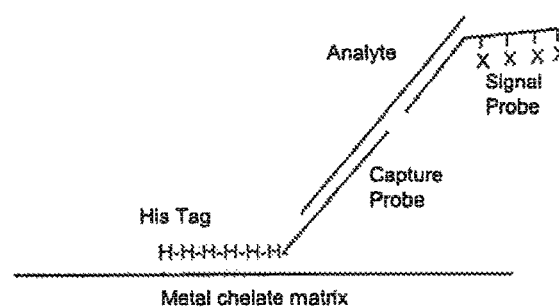

Detection of an analyte may also take place with unlabeled analytes by means of the additional use of a labeled probe that is complementary to the nucleic acid(s) of interest. This may be used with nucleic acids in their native forms, or complementary copies derived form copying or amplification procedures. A depiction of a format with this process is shown in FIG. 1C.

Figure 1D:
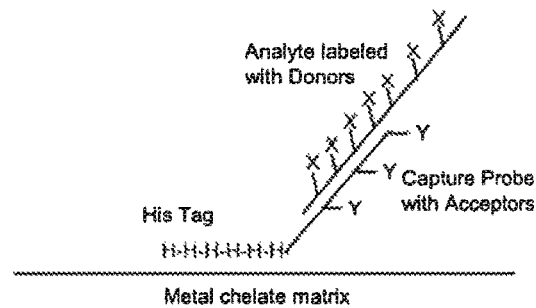
Figure 1E:
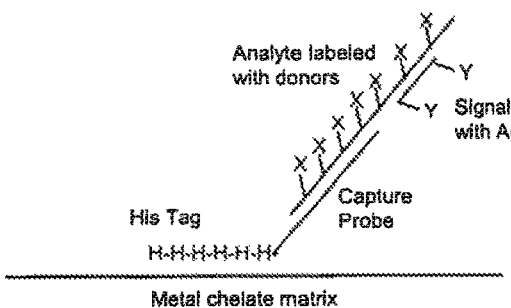
Figure 1F:
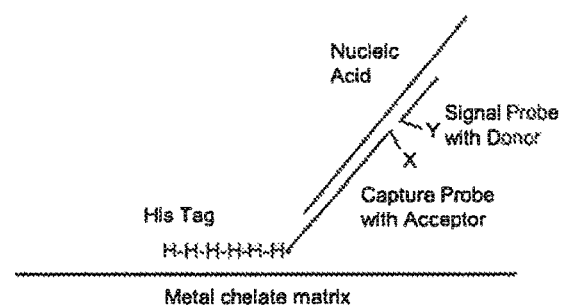

Other formats are also possible involving energy transfer elements where either a capture nucleic acid, an analyte or a probe is labeled with one or more energy transfer donors and one of the foregoing is labeled with an energy acceptor. Examples of various formats that could be used with this arrangement are shown in FIGS. 1D-1F. Thus, the compositions of the present invention can comprise one or more energy transfer donors, or one or more energy transfer acceptors.

The present invention and the above-described compositions can be used to isolate one or more species of a nucleic acid of interest. In one such process, various elements would be provided including a sample containing or suspected of containing the nucleic acid of interest, a composition which comprises a nucleic acid portion and a first member of an affinity binding pair, wherein the nucleic acid portion comprises sequences complementary to the nucleic acid species of interest, and the affinity binding pair comprises (a) a metal binding peptide and an immobilized metal, or (b) a peptide affinity group; and wherein the first member of the affinity binding pair being attached, for example, through a linker arm, to one or more nucleotides in said nucleic acid portion; and a matrix comprising a second member of the affinity binding pair. In this process, the composition hybridizes with any nucleic acid of interest contained in the sample to form a first complex. This is followed by contacting the first complex with the matrix provided to form a second complex by means of a binding interaction between the first member and the second member of the affinity binding pair. The material bound to the matrix could then be separated from unbound material, thereby isolating said nucleic acid species of interest. Thus, the portion of the sample that remains bound to the matrix can or may comprise the nucleic acid species of interest. Contrariwise, the portion of the sample that remains unbound to the matrix may or could comprise the nucleic acid species of interest. It should be understood to those skilled in the art that one or more washing steps could be used in the process just described above. The metal binding peptide, the immobilized metal, the peptide affinity group, linker arms, have been described above with respect to other descriptions of the present compositions and processes.

In a different application of the present invention, a process is provided for detecting the presence or quantity of a nucleic acid of interest. In this detection or quantification process, various elements are provided. These include a sample containing labeled nucleic acids, a composition comprising a nucleic acid portion and a first member of an affinity binding pair, wherein the nucleic acid portion comprises sequences complementary to the nucleic acid of interest, and a solid support or matrix comprising a second member of the affinity binding pair. The affinity binding pair can comprise: (a) a metal binding peptide and an immobilized metal, or (b) a peptide affinity group. The first member of the affinity binding pair is attached to one or more nucleotides of said nucleic acid portion, and this attachment can be through a linker arm as described in further detail above. Using the elements provided, the above composition is hybridized with any labeled nucleic acid of interest contained in the sample to form a first complex. This first complex is contacted with the matrix to form a second complex by means of a binding interaction between the first member and the second member of the affinity binding pair. The matrix is washed one or more times to remove unhybridized nucleic acids from the matrix. Detection or quantification of the nucleic acid of interest is carried out by means of detecting or quantifying a signal from the labels. Such labels are detectable fluorescently, chemiluminescently, colorimetrically or enzymatically. The just described process can include a further step of releasing the second complex from the matrix prior to detecting or quantifying the nucleic acid of interest. The nature of the metal binding peptide, the immobilized metal, the peptide affinity group, the linker arm, energy transfer donors and energy transfer acceptors have been described earlier in this disclosure and need not be reiterated here.

Other processes for detecting or quantifying nucleic acids of interest are also contemplated and provided by this invention. In one such detection or quantification process, the following elements are provided: a sample containing or suspected of containing the nucleic acid of interest; a labeled probe complementary to the nucleic acid of interest; a composition comprising a nucleic acid portion and a first member of an affinity binding pair, wherein the nucleic acid portion comprises sequences complementary to the nucleic acid of interest, wherein the affinity binding pair comprises (a) a metal binding peptide and an immobilized metal, or (b) a peptide affinity group, and wherein the first member of the affinity binding pair is attached, e.g., through a linker arm, to one or more nucleotides of said nucleic acid portion through a sugar, phosphate or base of the nucleotide or nucleotides; and a matrix comprising a second member of the affinity binding pair. In this process, any nucleic acids of interest in the sample are hybridized with labeled probe and the composition to form a first complex. This first complex is contacted with the matrix to form a second complex by means of a binding interaction between the first member and the second member of the affinity binding pair. The matrix can be washed one or more times to remove unbound materials from the sample. Detection or quantification of the nucleic acid of interest can be carried out by means of detecting or quantifying a signal from the labels. Such labels are detectable fluorescently, chemiluminescently, colorimetrically or enzymatically. An additional step of releasing the second complex from the matrix can be carried out or included in this process prior to carrying out detection or quantification.

In the process just described above, aspects such as the metal binding peptide, the immobilized metal, the peptide affinity group, the linker arm, energy transfer donors, energy transfer acceptors, and the like, have been described previously in this disclosure and will not be reiterated. With respect to the energy transfer elements, it should be understood that the labeled probes can comprise one or more energy transfer donors and the composition can comprise one or more energy transfer acceptors. Alternatively, the labeled probes can comprise one or more energy transfer acceptors and the composition can comprise one or more energy transfer donors. As a different variation, the labeled probes can comprise one or more energy transfer donors and the nucleic acids in the sample provided can be labeled with one or more energy transfer acceptors. Alternatively, in this different variation, the labeled probes can comprise one or more energy transfer acceptors and the nucleic acids in the sample provided can be labeled with one or more energy transfer donors.

In a different embodiment, the present invention and compositions can be directed to another process for detecting the presence or quantity of a nucleic acid of interest. Initially provided are several elements including: a sample containing or suspected of containing the nucleic acid of interest; a probe complementary to the nucleic acid of interest and comprising two portions, wherein a first comprises sequences complementary to the nucleic acid of interest, and a second portion comprising a signal sequence; a composition comprising a nucleic acid portion and a first member of an affinity binding pair, wherein the nucleic acid portion comprises sequences complementary to the nucleic acid of interest, wherein the affinity binding pair comprises (a) a metal binding peptide and an immobilized metal, or (b) a peptide affinity group, and wherein the first member of the affinity binding pair is attached, through a linker arm, for example, to one or more nucleotides of the nucleic acid; and a matrix comprising a second member of the affinity binding pair. Any nucleic acids of interest which are in the sample are allowed to hybridize with the labeled probe and the composition to form a first complex. Such first complex is contacted with the matrix to form a second complex by means of binding interactions between one or more binding partners and the affinity peptide. The matrix is washed in a single step or a series of washing steps to remove unbound materials from the sample. Detection or quantification of the nucleic acid of interest is carried out by hybridizing labeled oligonucleotides complementary to the signal sequence. The labeled oligonucleotides are detectable fluorescently, chemiluminescently, colorimetrically or enzymatically. The nature of the metal binding peptide, i.e., the amino acid sequences used therein, the immobilized metal, the peptide affinity group, and the like, have been previously described in this disclosure and will not be repeated here.

The signal sequence that may be used for this purpose have been described previously, including methods and compositions described by Pergolizzi et al., in European Publication No. 0 128 332 A1, based on U.S. patent application Ser. No. 06/491,929, filed May 5, 1983; and Urdea et al., U.S. Pat. No. 5,124,246. In this aspect of the present invention, such signal sequence can comprise a homopolymeric sequence, or it can comprise a heterologous sequence where the heterologous sequence is neither identical nor complementary to the nucleic acid of interest.

In another aspect of the present invention, the use of the kininogen peptide sequence is disclosed as being useful for incorporation into nucleic acids coding for proteins of interest. The provision of this novel affinity peptide may increase the range of fusion proteins that may be successfully designed with an affinity sequence. As mentioned earlier, even the flexibility of being able to use either the carboxy or amino terminus as an insertion site may be insufficient and both locations may interfere in either production or activity of the recombinant protein of interest. The availability of an alternative peptide sequence may allow generation of recombinant proteins that overcome this problem.

Other components or elements can be added to the just-described composition including one or more energy transfer donors or one or more energy transfer acceptors.

As such, this invention is also directed to and provides a fusion protein comprising a biologically active polypeptide or protein and at least one affinity peptide attached to the amino-terminus or the carboxyl-terminus of the biologically active polypeptide or protein, wherein the affinity peptide comprises at least a portion of the amino acid sequence of kininogen, the portion comprising a metal binding peptide. In a different aspect, the invention also provides a fusion protein comprising a biologically active polypeptide or protein and an affinity peptide attached at the amino-terminus and an affinity peptide attached at the carboxyl-terminus of the biologically active polypeptide or protein, wherein the affinity peptides comprise at least a portion of the amino acid sequence kininogen, the portion also comprising a metal binding peptide. A preferred sequence for the kininogen used as the affinity peptide in such fusion proteins is GHGLGHGHEQQHGLGHGHK (SEQ ID NO:10), or a portion thereof. The kininogen can be human kininogen if desired. Other aspects of the fusion proteins just described above should be noted. One aspect relates to the amino acid sequence between the biologically active polypeptide or protein and the affinity peptides, and this sequence is or can be recognizable by a protease, such as enterokinase or coagulation factor Xa. Further, the affinity peptide may bind nickel, copper, cobalt or zinc.

A format may be used where the affinity tagged antibody is specific for a unique target of interest where the target may be a protein or some other molecule of interest. This approach entails construction of a unique antibody for each antigen of interest and it has been previously described in the context of protein arrays by Wingren et al., (2005 Proteomics 5; 1281-1291) where a library of single-chain Fv antibodies were fixed to a matrix by either a metal or an anti-tag antibody. Other antibodies that have been modified this way have been described by Johnson et al. in U.S. Patent Application No. 2004/0197866 and Wu et al., in U.S. Patent Application No. 2006/0094062.

It should be appreciated that the present invention can be used to provide a process for modifying proteins of interest. To modify such a protein, three elements are provided including: (i) a nucleic acid that codes for the protein of interest; (ii) a nucleic acid that codes for a portion of the amino acid sequence of kininogen, wherein the portion codes for a metal binding peptide; and (iii) an expression vector. To modify the protein with the elements provided, the nucleic acid (ii) is added to the nucleic acid (i) to generate a nucleic acid coding for a fusion protein. The fusion protein coding nucleic acid is inserted into the expression vector (iii), thereby generating a vector that expresses the modified protein of interest. Other aspects of the just described protein modification process deserve mention. One aspect concerns the expression vector (iii) and it can comprise a number of different types, including a mammalian expression vector, a bacterial expression vector, an insect cell expression vector and a yeast expression vector. The expression vector (iii) can be plasmid or a viral vector.

Thus, this invention when applied to the isolation of a protein of interest, provides the following process. Several elements are provided including (i) a nucleic acid that codes for the protein of interest; (ii) a nucleic acid that codes for a portion of the amino acid sequence of kininogen, wherein that portion codes for a metal binding peptide; (iii) an expression vector; and (iv) a metal-modified matrix. To isolate the protein of interest, the nucleic acid (ii) is added to the nucleic acid (i) to generate a nucleic acid coding for a fusion protein. The nucleic acid coding for the fusion protein is inserted into the expression vector (iii), resulting in the expression of the protein of interest. Purification can be carried out by binding the protein of interest to the metal-modified matrix (iv). This can be desirably performed using a chromatographic column or a microtitre plate as the metal-modified matrix. As described previously, the expression vector (iii) can comprise a mammalian expression vector, a bacterial expression vector, an insect cell expression vector or a yeast expression vector. The expression vector (iii) can also be a plasmid or a viral vector.

In another embodiment of the present invention, a method of isolation or detection of proteins is described. As described earlier, the incorporation of an amino sequence for an affinity tag has been incorporated into proteins to effect an ease of isolation. However, this entails a genetic modification of the protein of interest and it has become clear that even with a flexibility of being able to add to either the carboxy or the amino end, some proteins lose functionality by such means. This system does not allow the detection of unaltered or native proteins. Accordingly, it is disclosed herein that an antibody to a protein can be engineered to have an amino sequence that comprises an affinity peptide, thus allowing capture of the antibody onto a solid matrix as well as any complex formed between the modified antibody and its target. This will be of special use and significance when the target is a protein that is desired to be isolated.

On the other hand, a more universal reagent can be made by construction of a tagged antibody that has an affinity for other antibodies. Thus, for example, an anti-goat antibody that is derived from mouse cells can be redesigned to comprise an affinity peptide and used to collect complexes that are made of goat antibodies that are bound to their particular analyte targets. This system uses a universal reagent in that only the anti-goat antibody needs to be modified and this reagent should be able to recognize a wide variety of complexes formed between goat antibodies and their antigen targets. Thus, the need for individually modifying each antibody used for as an antibody/antigen pair is obviated. Although this method can subsequently be used to isolate the antigen target by appropriate release of the target, it is understood that the present invention may also be used in formats that are used to detect or quantify targets by means of immunoassays. It is understood that when the terms "antibody" or "antibodies" are used in the present invention, such terms include, without limitation, antibody fragments, single chain antibodies, and the like.

This invention further provides a fusion protein comprising an antibody and at least one affinity peptide attached to the amino terminus or the carboxyl terminus of the antibody, wherein the affinity peptide comprises a metal binding peptide or is one member of a peptide affinity group. The antibody has an affinity for a different antibody in this case. A different embodiment provided by the present invention is a fusion protein comprising an antibody and an affinity peptide attached to the amino terminus and an affinity peptide attached to carboxyl terminus of the antibody. The affinity peptide comprises a metal binding peptide or is one member of a peptide affinity group, wherein the antibody has an affinity for a different antibody. In the case of either fusion protein, the peptide affinity group can comprise S-protein and S-peptide, GST and GSH, PKA peptide and PKA, HA peptide and HA, KSI and oligo PHE, KSI and oligo Leu, oligo Arg and oligo Glu, or oligo Arg and oligo Asp. Additionally, the metal binding peptide can comprise oligohistidine or an oligopeptide comprising any of the following sequences: HGGHHG (SEQ ID NO:1), SPHHG (SEQ ID NO:2), SPHHGGSPHHG (SEQ ID NO:3), HPHHG (SEQ ID NO:4), HPHHGGHPHHG (SEQ ID NO:5), SPHHGGHPHHG (SEQ ID NO:6), HPHHGGSPHHG (SEQ ID NO:7), KDHLIHNVHKEEHAHAHNK (SEQ ID NO:8), GHGLGHGHEQQHGLGHGHK (SEQ ID NO:10), or HGLGHGHEQQHGLGHGH (SEQ ID NO:9).

Processes for analyte isolation and detection or quantification are also provided by the present invention. To isolate an analyte of interest, the following process can be used in accordance with this invention. Four elements are initially provided, including (i) a sample containing or suspected of containing the analyte of interest; (ii) a first antibody having an affinity for the analyte; (iii) a fusion antibody comprising: (a) an antibody and at least one affinity peptide attached to the amino terminus or the carboxyl terminus of the antibody, wherein the affinity peptide comprises a metal binding peptide or is one member of a peptide affinity group, wherein the antibody has an affinity for a different antibody; or (b) an antibody and an affinity peptide attached to the amino terminus and an affinity peptide attached to carboxyl terminus of the antibody, wherein the affinity peptide comprises a metal binding peptide or is one member of a peptide affinity group, wherein the antibody has an affinity for a different antibody; and (iv) a matrix comprising a metal or a second member of the affinity peptide group.

In this analyte isolation process, the sample is allowed to contact the first antibody, thereby forming a first complex between the first antibody and any analyte present in the sample. The first complex is allowed to contact with the fusion antibody, thereby forming a second complex between the first complex and the fusion antibody. The second complex is contacted with the matrix to bind the second complex to the matrix. Unbound material is removed from the matrix, and the analyte of interest is released from the second complex, thereby isolating the analyte of interest.

In this analyte isolation process, other aspects can be described. For example, the peptide affinity group can comprise S-protein and S-peptide, GST and GSH, PKA peptide and PKA, HA peptide and HA, KSI and oligo PHE, KSI and oligo Leu, oligo Arg and oligo Glu, or oligo Arg and oligo Asp. Further, the metal binding peptide can comprise oligohistidine or an oligopeptide comprising any of the sequences: HGGHHG (SEQ ID NO:1), SPHHG (SEQ ID NO:2), SPHHGGSPHHG (SEQ ID NO:3), HPHHG (SEQ ID NO:4), HPHHGGHPHHG (SEQ ID NO:5), SPHHGGHPHHG (SEQ ID NO:6), HPHHGGSPHHG (SEQ ID NO:7), KDHLIHNVHKEEHAHAHNK (SEQ ID NO:8), GHGLGHGHEQQHGLGHGHK (SEQ ID NO:10), or HGLGHGHEQQHGLGHGH (SEQ ID NO:9).

Analyte detection or quantification can also be carried out in accordance with this invention. In a process for detecting or quantifying an analyte of interest, e.g., a protein or a polypeptide, the following elements are provided: (i) a labeled sample containing or suspected of containing labeled analyte of interest; (ii) a first antibody having an affinity for the analyte; (iii) a fusion antibody comprising: (a) an antibody and at least one affinity peptide attached to the amino terminus or the carboxyl terminus of the antibody, wherein the affinity peptide comprises a metal binding peptide or is one member of a peptide affinity group, wherein the antibody has an affinity for a different antibody; or (b) an antibody and an affinity peptide attached to the amino terminus and an affinity peptide attached to carboxyl terminus of the antibody, wherein the affinity peptide comprises a metal binding peptide or is one member of a peptide affinity group, wherein the antibody has an affinity for a different antibody; and (iv) a matrix comprising a metal or a second member of the affinity peptide group. The sample is contacted with the first antibody, thereby forming a first complex between the first antibody and any analyte present in the sample. The first complex so formed is contacted with the fusion antibody, thereby forming a second complex between the first complex and the fusion antibody. The second complex is contacted with the matrix to bind the second complex to the matrix. Unbound material is removed from the matrix. Detection or quantification of the labeled analytes bound to the matrix is performed by means of detecting or quantifying a signal from the labels. The labels are detectable fluorescently, chemiluminescently, colorimetrically or enzymatically. It should also be noted that an additional step can be performed in connection with this process, namely, the analyte of interest can be released from the second complex prior to performing any detection or quantification. As previously described, the peptide affinity group can comprise S-protein and S-peptide, GST and GSH, PKA peptide and PKA, HA peptide and HA, KSI and oligo PHE, KSI and oligo Leu, oligo Arg and oligo Glu, or oligo Arg and oligo Asp. Further, the metal binding peptide can comprise oligohistidine or an oligopeptide comprising any of the sequences: HGGHHG (SEQ ID NO:1), SPHHG (SEQ ID NO:2), SPHHGGSPHHG (SEQ ID NO:3), HPHHG (SEQ ID NO:4), HPHHGGHPHHG (SEQ ID NO:5), SPHHGGHPHHG (SEQ ID NO:6), HPHHGGSPHHG (SEQ ID NO:7), KDHLIHNVHKEEHAHAHNK (SEQ ID NO:8), GHGLGHGHEQQHGLGHGHK (SEQ ID NO:1), or HGLGHGHEQQHGLGHGH (SEQ ID NO:1).

This invention also provides a process for detecting and quantifying an analyte of interest, such as a protein or polypeptide. In such a process, the following elements are provided: (i) a labeled sample containing or suspected of containing labeled analytes of interest; (ii) a first antibody having an affinity for the analyte; (iii) a fusion antibody comprising: (a) an antibody and at least one affinity peptide attached to the amino terminus or the carboxyl terminus of the antibody, wherein the affinity peptide comprises a metal binding peptide or is one member of a peptide affinity group, wherein the antibody has an affinity for a different antibody; or (b) an antibody and an affinity peptide attached to the amino terminus and an affinity peptide attached to carboxyl terminus of the antibody, wherein the affinity peptide comprises a metal binding peptide or is one member of a peptide affinity group, wherein the antibody has an affinity for a different antibody; and (iv) a matrix comprising a metal or a second member of the affinity peptide group. In this detection or quantification process, a first complex is formed among the matrix, the fusion antibody and the first antibody. The first complex is contacted with the labeled sample to form a second complex between the first complex and any labeled analytes that may be present in the sample. Unbound material is removed from the matrix. Labeled analytes bound to the matrix are detected or quantified by means of detection or quantification of the signal generated from the labels. Such labels are detectable fluorescently, chemiluminescently, colorimetrically or enzymatically. Furthermore, the matrix can comprise an array of different first antibodies, thereby allowing for detection or quantification of multiple analytes of interest.

The examples which follow are set forth to illustrate various aspects of the present invention but are not intended

DESCRIPTION OF THE PREFERRED EMBODIMENTS

The following are examples illustrating the present invention.

Example 1

Preparation of Oligonucleotide Modified with Oligohistidine

Step 1 Synthesis of N-Trifluoroheptahistidine —NHS Ester 32 mg (~30 µMoles) of acetylated heptahistidine (Biopeptides, Inc. San Diego Calif.) were dissolved in 200 µl methanol followed by addition of 400 µl of methyltrifluoroacetate and 50 µl of pyridine and the mixture left overnight at room temperature. The liquid phase was evaporated by a stream of argon and then evaporated in vacuo overnight to remove any traces of pyridiniumtrifluoroacetate formed by the presence of trifluoroacetic acid contaminants in the methyltrifluoroacetate. The residue was dissolved in 200 µl of dimethylformamide (DMF) followed by the addition of 60 µmoles of n-hydroxysuccinimide and then 50 µl of 0.9 M dicyclohexylcarbodiimide in DMF. The mixture was stirred overnight and a urea precipitate was removed by centrifugation.

Step 2 Preparation of Amine Modified Rhodamine Labeled Oligonucleotide

A 5' amino modified oligonucleotide was ordered from Sigma Genosys (Sigma-Aldrich, St. Louis, Mo.) with the following sequence: 5' amine-tcaaccaac 3'. The oligonucleotide was labeled by terminal transferase using a 3'-Oligonucleotide labeling system (Enzo Life Sciences Inc, Farmingdale, N.Y.) and rhodamine labeled dUTP (Enzo Life Sciences Inc, Farmingdale, N.Y.).

Step 3 Addition of the Oligohistidine Peptide to the Rhodamine Labeled Oligonucleotide.

100 µg of the oligo prepared in step 2 was phenol extracted, ethanol precipitated and dissolved in 200 µl of 0.2M Sodium Borate, 5 mM EDTA, pH 8.5 followed by addition of 300 µl of DMF and 50 µl of the N-trifluoroheptahistidine —NHS ester synthesized in step 1. The mixture was stirred overnight and the derivatized DNA was then precipitated by the addition of 10 volumes of n-butanol. The pellet was dissolved in 200 ul of 1M Lithium Hydroxide solution and left at room temperature for 30 minutes to remove the trifluoroacetyl groups. The heptahistidine modified DNA was then precipitated with 10 volumes of ethanol and redissolved in binding buffer (20 mM Phosphate, 500 mM NaCl, pH 7.4)

Example 2

Efficiency of Binding and Release of Oligohisitidine Modified Oligonucleotide to Nickel Coated Sepharose Beads (Ni-Column)

The heptahistidine modified rhodamine oligonucleotide from Example 1 was diluted in binding buffer (20 mM Phosphate, 500 mM NaCl, pH 7.4) and added to a Ni-column (Ni Sepharose high performance, GE Healthcare, Piscataway, N.J.). As a control, rhodamine labeled oligonucleotide without the addition of the heptahistidine was also added to a Ni-column. The columns were then washed with 8 volumes of binding buffer followed by a 5 volumes of binding buffer containing 0.5 M Imidazole to release the oligonucleotide histidine groups and the eluants collected. Quantification was carried out using a spectrofluorometer (Ex: 556 nm, Em: 580) for both the Effluent (Ft) that did not bind and for the Eluent (Elu) that was released after binding.

Figure 2A:
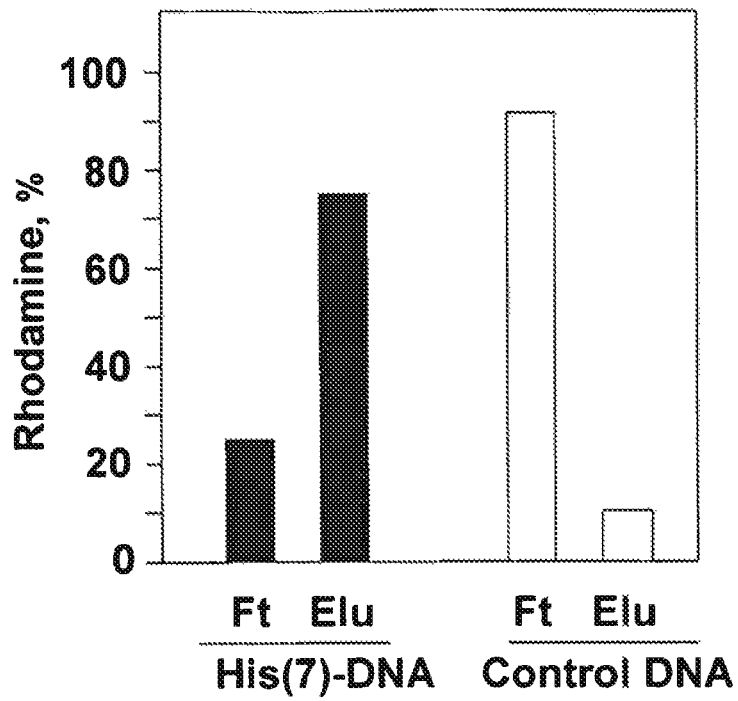
FIGS. 2A and 2B illustrate binding of chimeric constructs to matrices, as follows.

The results of this experiment are shown in FIG. 2(A) as represented by the percentage of the rhodamine signal of the input material. In this experiment 75% of the oligohistidine modified oligonucleotide bound to the column while only 8% of the unmodified rhodamine oligonucleotide remained bound. The lack of quantitative binding by the oligohistidine modified preparation is likely to be an indication that not all of the oligonuclotides were conjugated to the peptide. This was confirmed by taking the effluent that was unable to bind and running it a second time over the Ni-column where the level of binding was observed to be the same as previously observed with the oligonucleotide lacking the histidine (data not shown).

Example 3

Figure 2B:
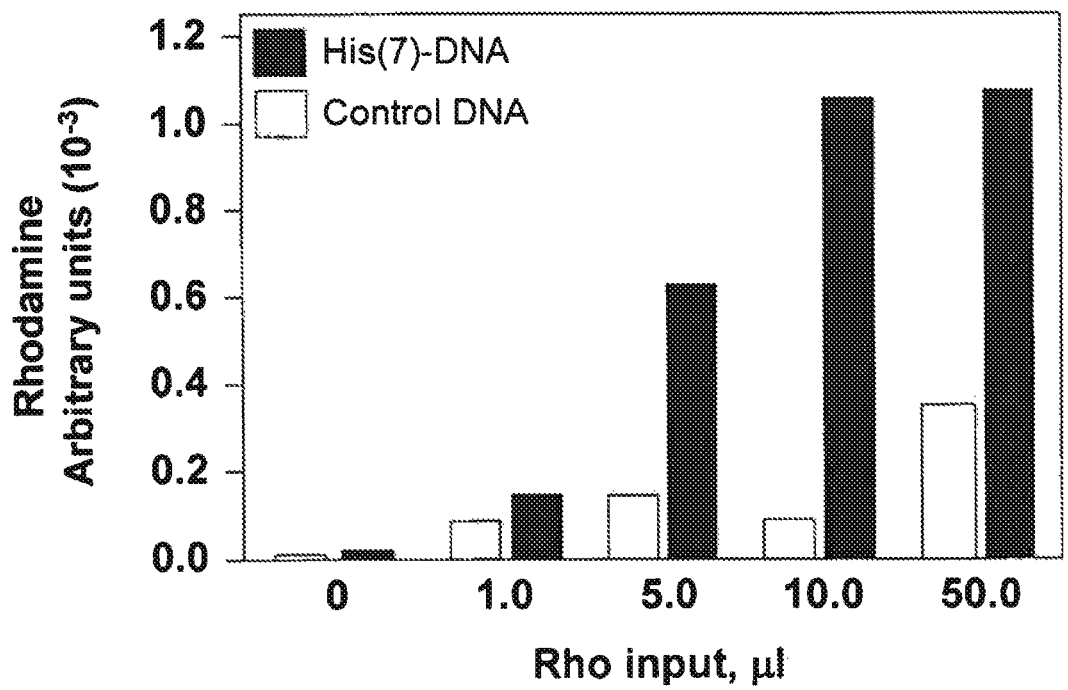

Efficiency of Binding of Oligohistidine Modified Oligonucleotide to Nickel Coated 96-Well Plates Binding of the oligohistidine modified oligonucleotide to a matrix was also tested by binding to 96 well plates instead of the columns used in Example 2. Identical dilutions of histidine modified and unmodified rhodamine labeled oligonucleotides from Example 2 were added to Nickel-coated plates (HisGrab Nickel coated 96-well plates, Pierce, Rockford, Ill.) and incubated for 3 hours at room temperature, followed by washing 3 times with 200 ul binding buffer. The bound DNA was measured by detecting rhodamine with a plate reader (filters: Ex550, Em610, Fluostar Optima, BMG Labtech). Results of this experiment are shown in FIG. 2(B). The Histidine-modified DNA bound to the Ni-plates more effectively than the control DNA. For example, an input of 10 ul of control and His(7)-DNA showed 90% of the histidine modified DNA being bound to the wells, while only 10% of the control DNA was detected. The results shown in FIG. 2 (B) also indicate that with the highest input level (50 ul), the wells were overloaded.

Example 4

Effects of Other Reagents on Binding

Figure 3:
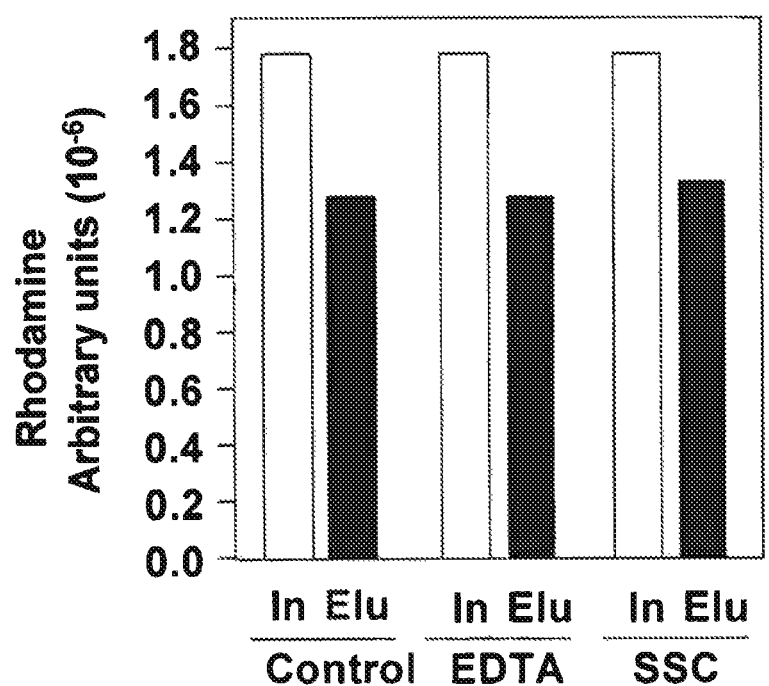
FIG. 3 illustrates the effects of various reagents on binding of chimeric constructs.

Preparations of nucleic acids are commonly taken up in the presence of chelators such as EDTA or SSC (standard saline citrate). Since it is possible that these could be competitors for a peptide/chelate interaction, the oligonucleotides from Example 1 were tested for the ability to be bound in their presence. The histidine modified oligos were incubated with Ni beads in the presence of binding buffer (control), or binding buffer with either 0.5 mM EDTA or 1×SSC. The results of this Experiment are shown in FIG. 3, where it can be seen that the presence of at least low levels of these components had no effect on the efficiency of binding of the oligohistidine modified nucleic acid.

Many obvious variations will be suggested to those of ordinary skill in the art in light of the above detailed descriptions of the present invention. All such obvious variations are fully contemplated and are embraced by the scope and spirit of the present invention as set forth in the claims that now follow.

What is claimed is:

1. A composition of matter, comprising:
    a chimeric molecule comprising
        a polynucleic acid portion comprising one or more energy transfer donors or energy transfer acceptors, and
        a peptide affinity tag portion covalently attached to the polynucleic acid portion;
    a first polynucleic acid molecule hybridized to the polynucleic acid portion of the chimeric molecule; and
    a second polynucleic acid molecule hybridized to the first polynucleic molecule and not to the polynucleic acid portion of the chimeric molecule, said second polynucleic acid comprising one or more energy transfer donors or energy transfer acceptors,
wherein when the polynucleic acid portion comprises one or more energy transfer donors, the second polynucleic acid molecule comprises one or more energy transfer acceptors and when the polynucleic acid portion comprises one or more energy transfer acceptors, the second polynucleic acid molecule comprises one or more energy transfer donors.

2. The composition of matter of claim 1, wherein the polynucleic acid portion of the chimeric molecule and the peptide affinity tag portion of the chimeric molecule are covalently attached through a linker arm.

3. The composition of matter of claim 1, wherein the peptide affinity tag portion comprises a metal-binding peptide affinity tag.

4. The composition of matter of claim 3, wherein the polynucleic acid portion of the chimeric molecule and the peptide affinity tag portion of the chimeric molecule are covalently attached through a linker arm.

5. The composition of claim 3, further comprising an immobilized metal wherein the metal-binding affinity tag is bound to the immobilized metal.

6. The composition of matter of claim 5, wherein the polynucleic acid portion of the chimeric molecule and the peptide affinity tag portion of the chimeric molecule are covalently attached through a linker arm.

* * * * *

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Gly Gly His His Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Pro His His Gly
1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Pro His His Gly Gly Ser Pro His His Gly
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Pro His His Gly
1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Pro His His Gly Gly His Pro His His Gly
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                             peptide

<400> SEQUENCE: 6

Ser Pro His His Gly Gly His Pro His His Gly
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Pro His His Gly Gly Ser Pro His His Gly
1               5                   10

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Asp His Leu Ile His Asn Val His Lys Glu Glu His Ala His Ala
1               5                   10                  15

His Asn Lys

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Gly Leu Gly His Gly His Glu Gln Gln His Gly Leu Gly His Gly
1               5                   10                  15

His

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly His Gly Leu Gly His Gly His Glu Gln Gln His Gly Leu Gly His
1               5                   10                  15

Gly His Lys

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

```
His His His His His His
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His His His His His His His
1               5
```